(12) United States Patent
Link et al.

(10) Patent No.: US 10,973,643 B2
(45) Date of Patent: Apr. 13, 2021

(54) JOINT CONFIGURATION

(71) Applicant: Waldemar Link GmbH & Co. KG, Hamburg (DE)

(72) Inventors: Helmut D. Link, Hamburg (DE); Jörg Ewald, Hamburg (DE); Günther Jendro, Kaltenkirchen (DE); Andreas Dänike, Henstedt-Ulzburg (DE); Udo Borchers, Norderstedt (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 18 days.

(21) Appl. No.: 16/082,954

(22) PCT Filed: Mar. 6, 2017

(86) PCT No.: PCT/EP2017/055165
§ 371 (c)(1),
(2) Date: Sep. 7, 2018

(87) PCT Pub. No.: WO2017/153322
PCT Pub. Date: Sep. 14, 2017

(65) Prior Publication Data
US 2019/0099275 A1      Apr. 4, 2019

(30) Foreign Application Priority Data
Mar. 9, 2016 (EP) ..................................... 16159418

(51) Int. Cl.
*A61F 2/38* (2006.01)
*A61F 2/30* (2006.01)

(52) U.S. Cl.
CPC .............. *A61F 2/385* (2013.01); *A61F 2/384* (2013.01); *A61F 2002/30367* (2013.01);
(Continued)

(58) Field of Classification Search
CPC .. A61F 2002/30492; A61F 2002/30632; A61F 2002/30367; A61F 2002/30672; A61F 2/38; A61F 2/3836
See application file for complete search history.

(56) References Cited

U.S. PATENT DOCUMENTS 8,795,387 B1 * 8/2014 Razink .................... A61F 2/585
623/62
9,827,105 B2 * 11/2017 Sass ...................... A61F 2/3845
2014/0025172 A1 1/2014 Montgomery et al.

FOREIGN PATENT DOCUMENTS

FR          2935894 A1    3/2010
RU            37931 U1    5/2004
(Continued)

*Primary Examiner* — Brian A Dukert
*Assistant Examiner* — Amanda M Barkan
(74) *Attorney, Agent, or Firm* — Edwin A. Sisson, Attorney at Law; Jeffrey J. Banyas (57) ABSTRACT

A joint configuration is proposed for a joint endoprosthesis forming a hinge joint, comprising a joint receptacle, which has a joint receptacle surface and a receptacle locking structure, and a joint body, which is receivable in the joint receptacle and has a joint body surface and a body locking structure. The joint receptacle surface and the joint body surface are movable in relation to one another into a position in which the receptacle locking structure and the body locking structure assume a locked position, in which they can be engaged for a locked state between the joint receptacle and the joint body.

13 Claims, 4 Drawing Sheets

(52) U.S. Cl.
CPC ............ *A61F 2002/30387* (2013.01); *A61F 2002/30433* (2013.01); *A61F 2002/30492* (2013.01); *A61F 2002/30607* (2013.01); *A61F 2002/30616* (2013.01); *A61F 2002/30632* (2013.01); *A61F 2002/30672* (2013.01)

(56) References Cited

FOREIGN PATENT DOCUMENTS

| RU | 51490 U1 | 2/2006 |
| RU | 60344 U1 | 1/2007 |
| RU | 2380061 C1 | 1/2010 |
| RU | 2433803 C1 | 11/2011 |
| WO | 2006/087582 A1 | 8/2006 |
| WO | 2013/144392 A1 | 10/2013 |

* cited by examiner

JOINT CONFIGURATION

PRIORITIES AND CROSS REFERENCES

This application claims priority from International Application No. PCT/EP2017/055165 filed on 6 Mar. 2017 which claims priority from European Application No. EP 16159418.9 filed on 9 Mar. 2016, the teachings of each of which are incorporated by reference herein in their entirety.

FIELD OF THE INVENTION

The present invention relates to a joint configuration for a joint endoprosthesis forming a hinge joint and a method for its locking.

PRIOR ART

It can be necessary or advantageous to immobilize a joint in the context of a treatment. Indications for this which require such an immobilization of a joint are, for example, inflammations in the region of the joint, weakening or irritation of the ligament apparatus which surrounds the joint, or a fracture of the bone tissue.

An immobilization of a joint can also be advantageous in this case in conjunction with an artificial joint, which is already implanted or is still to be implanted. In particular in the case of an inflammation in the joint region which can be induced, for example, by a worn-out native joint, the problem moreover arises that inflamed tissue has to be removed, but a joint replacement is not yet supposed to be implanted, because its mobility would result in a further irritation of the surrounding tissue.

For this reason, instead of a complete joint replacement, for example, an arthrodesis nail is at least temporarily implanted, which blocks the affected joint by bridging it, for example. As soon as the health situation of the patient has sufficiently improved, the arthrodesis nail can be removed again in a further intervention and replaced by a joint replacement. For this purpose, the arthrodesis nail has to be removed again, which results in a further stress to the patient. Overall, two significant interventions are therefore necessary to treat the patient.

If an artificial joint replacement is already implanted, an inflammation of the surrounding bone or soft tissue or wear can make a revision of this joint necessary. The revision of a joint is also a relatively significant intervention, which strongly stresses the tissue of the patient and is frequently linked to a substantial loss of bone tissue. It is therefore advantageous under certain circumstances to also immobilize the joint here by means of an arthrodesis nail. The above-described two interventions are again the consequence.

Furthermore, after an implantation of an artificial joint or after its revision, an initial immobilization of the new artificial joint can additionally facilitate the healing, since the weakened ligament apparatus and the bone tissue can recover from the intervention. Lesser irritations and infections can also occur directly after an implantation of an artificial joint, which do not require a revision, but can be better treated by a temporary immobilization. There is presently no practical solution for this purpose to the knowledge of the inventor, except for ordering bed rest for the patient and thus accordingly strongly restricting his or her freedom of movement.

SUMMARY OF THE INVENTION

Proceeding therefrom, it was a problem of the present invention to provide a possibility which enables the most careful possible immobilization of the joint region without having to restrict the mobility of a patient excessively strongly.

The solution found for this is defined by the joint configuration according to claim 17 and the locking of a joint configuration according to claim 31. In this case, the respective dependent claims define preferred embodiments of the joint configuration or the locking method, respectively.

The joint configuration of the present invention for a joint endoprosthesis forming a hinge joint has in this case a joint receptacle comprising a joint receptacle surface and a receptacle locking structure and also a joint body, which is receivable in the joint receptacle and in turn has a joint body surface and a body locking structure. The joint receptacle surface and the joint body surface are movable in relation to one another into a position in which the receptacle locking structure and the body locking structure assume a locking position, in which they can be engaged for a locked state between the joint receptacle and the joint body.

The joint endoprosthesis can be immobilized by this joint configuration and accordingly has the effect of an arthrodesis nail in the locked state. The rotation of the hinge joint is thus prevented. Moreover, by disengaging the locking, this blockage of the joint configuration and thus of the joint endoprosthesis can be canceled out again. As a result, an irritation or inflammation of the affected joint is treated without a revision of the joint endoprosthesis being necessary.

Furthermore, the joint configuration has the advantage in particular that locking of the hinge joint is possible by way of a small incision into the tissue of the patient, which makes the body locking structure and the receptacle locking structure accessible. Such a minimally-invasive intervention minimizes the stress to the patient.

Moreover, pain which could otherwise be induced by the normal mobility of the joint is prevented by the blocking of the joint. A patient is thus capable of again covering short distances himself or herself, without requiring external aid in this case.

In the hinge joint, the joint body forms the axis of the hinge joint and the joint receptacle forms the bearing for this axis. Such hinge joints occur in animals or in humans, for example, in the knee joint or in the elbow joint. The use of the term patient is accordingly not to be interpreted as restricted to humans.

In one preferred embodiment, the receptacle locking structure adjoins the joint receptacle surface and the body locking structure adjoins the joint body surface.

Such an arrangement of the receptacle locking structure and the body locking structure has the advantage that the locking takes place in the immediate vicinity of the running surface of the hinge joint and thus particularly little play is achieved in the locked state, since the locking takes place where the joint obtains its mobility via the running surfaces. The movement of the joint is thus prevented precisely where it occurs. Due to the lesser play enabled in this way, possible failure of the locking is moreover prevented.

In a further particularly preferred embodiment, the receptacle locking structure is formed as a recess in the joint receptacle surface and/or the body locking structure is formed as a recess in the joint body surface.

Locking at the running surfaces of the joint with little play is also achieved in this embodiment.

If the body locking structure and the receptacle locking structure are formed complementary to one another, locking is carried out by direct interlocking between the two locking structures.

In a further embodiment, the receptacle locking structure and the body locking structure can be engaged using a locking element, wherein the locking element is preferably insertable in the locking position into the receptacle locking structure and the body locking structure.

In this embodiment, the receptacle locking structure and the body locking structure are therefore indirectly engaged with one another.

The locking element has the advantage that it does not remain in the joint configuration when no locking of the joint configuration is desired. In other words, it is a separate locking element. Therefore, on the one hand, the design of the joint configuration is simplified and, on the other hand, the possibility is prevented that the locking element unintentionally locks the joint. In this embodiment, the locking element is embodied so it can not only be disengaged but also removed. The above-described small incision in the vicinity of the joint is also sufficient here to execute the locking and cancel it out again.

Furthermore, in this embodiment, preferably both the receptacle locking structure and also the body locking structure are formed as recesses. The two recesses together form a locking recess in the locking position. In other words, the receptacle locking structure and the body locking structure align with one another in the locking position in such a manner that a locking element is insertable. The locking recess formed by the receptacle locking structure and the body locking structure is preferably rotationally symmetrical, more preferably cylindrical, and most preferably circularly cylindrical. Furthermore, the recesses preferably extend into the respective surface, and therefore a locking element can be inserted from outside the surface.

In a further preferred embodiment, the joint receptacle and the joint body are pivotable relative to one another about an axis of rotation and the locking element is insertable substantially parallel to the axis of rotation.

In this embodiment, a particularly simple access to the joint from lateral or medial for locking or unlocking of the joint from the outside is enabled by the ability to insert the locking element parallel to the axis of rotation of the hinge joint.

In a further preferred embodiment, the joint body has a securing section for securing the joint body on a first joint component, wherein the securing section is preferably formed as at least one flange at one end of the joint body.

The securing section prevents a separation of the joint body and the joint receptacle after an assembly and thus ensures a correct function of the joint configuration. Moreover, the securing section can be embodied in such a way that it is used as a stop, which enables a defined insertion during the assembly of the joint configuration.

The securing section is preferably formed as a flange, which is attached to at least one end of the joint body in the direction of the axis of rotation. The flange is preferably integrally connected to the flange. Securing of the securing section and thus of the joint body can therefore be carried out by attaching the securing section to a first joint component.

It is possible to provide flanges on both sides on the joint body in the axial direction, which prevent a separation of the joint body from the joint receptacle in the assembled state on both sides of the joint receptacle. In this case, the joint body can only be secured in the axial direction in the unlocked state by the two flanges and can rotate about the axis of rotation of the hinge joint and in relation to the first joint component.

In one particularly preferred embodiment, the securing section is fastened on the first joint component using a fastening element.

Complete securing of the joint body on the first joint component therefore takes place via at least one fastening element, i.e., it is secured against slipping out axially and also rotating in relation to the first joint component. The securing section can accordingly be formed in this embodiment by only one flange, which makes a compact construction of the joint configuration possible.

The complete securing via the fastening element preferably takes place in this case outside the joint axis and can be embodied most simply via a threaded connection.

In a further particularly preferred embodiment, at least one adapter element, which has a support surface for supporting the joint body surface, is provided between the joint body and the first joint component.

The use of an adapter element between the joint body and the first joint component enables the retrofitting of an already implanted joint endoprosthesis with the joint configuration. This has the advantage that an already implanted component of the joint endoprosthesis does not have to be removed from the bone and thus protects the patient. The joint configuration thus forms a reasonable supplementation to existing joint implant systems and expands the usage options thereof.

In the locked state, in a joint configuration provided with an adapter, a relative rotation between the joint receptacle and the adapter is preferably prevented.

In a further embodiment, the adapter element has a catch, which prevents a rotation between the adapter element and the first joint component.

This catch prevents a rotation between the adapter element and the first joint component both in the unlocked state and also in the locked state. The catch is preferably formed in the form of two stop surfaces, which interact in the assembled state with two stop surfaces of the first joint component in the rotational direction. The catch therefore ensures that locking takes place continuously between the joint receptacle and the first joint component.

Moreover, the locking angle between the joint receptacle and the first joint component can be selected via the catch via its corresponding arrangement. For example, it can be advantageous for a patient that the locking takes place in the case of a knee joint in a position of the joint configuration in which the patient is seated. This applies in particular to patients who use a wheelchair.

In a further particularly preferred embodiment, the locking element is preferably fixable in relation to the joint body via a threaded section.

Via such a threaded section, the locking element can be secured in relation to the joint configuration when it is in the inserted state for locking of the hinge joint. Intentional or unintentional moving out of the locking element is thus prevented. In particular in the case of an insertion of the locking element parallel to the axis of rotation of the hinge joint, the fixing via the threaded section can take place by simply screwing the locking element into a joint component i.e., the joint side of the joint receptacle or the joint body, an adapter element, and/or a securing section.

In a further particularly preferred embodiment, the joint receptacle has a connecting section for a connection to a second joint component.

The same advantage is achieved with this embodiment as in the case of the above-described adapter element. More precisely, it is possible in this embodiment to retrofit the joint configuration in the case of a second joint component which is functionally opposite to the first joint component. A revision of an already implanted joint component can therefore also be omitted here.

In a further particularly preferred embodiment, the joint configuration has a further receptacle locking structure and/ or a further body locking structure, which is arranged to provide at least one further locking position for locking of the joint configuration.

In this embodiment, it is possible to carry out the locking of the joint configuration and thus of the joint replacement in different angle positions. The locking angle can therefore be adapted to the respective requirements of the patient. It is thus not always advantageous, for example, to perform locking in such a way that the affected limb is in an extended state, for example, in the case of the above-mentioned use of a wheelchair.

In this case, two, three, or four receptacle locking or body locking structures are particularly preferably provided, which can only be moved with one of the respective other structures into a corresponding number of locking positions.

Furthermore, the present invention provides a method for locking a joint configuration for a joint endoprosthesis forming a hinge joint, wherein the method comprises the following steps. In one step, the insertion of a joint body is carried out, which has a joint body surface and a body locking structure, into a joint receptacle, which has a joint receptacle surface and a receptacle locking structure. Furthermore, the method provides a movement of the joint body surface and the joint receptacle surface in relation to one another, in such a way that the body locking structure and the receptacle locking structure assume a locking position. As part of the method, the locking of the joint body and the joint receptacle in the locking position is carried out by engaging the body locking structure and the receptacle locking structure.

This structure therefore enables a locking of a joint endoprosthesis and makes the much more complex use superfluous, which is much more stressful to the patient, of an arthrodesis nail. Moreover, the locking is preferably provided so it can be disengaged, and therefore after reaching the treatment goal, which is supposed to be achieved by the locking, the locking can be canceled out again and the patient can again use the joint endoprosthesis as such.

In a further embodiment of the method for installing a joint configuration, the locking takes place between the body locking structure and the receptacle locking structure using a locking element.

The use of a locking element for locking the joint configuration has in particular the above-described advantage that only a minimally-invasive intervention is required for the locking. If the locking element is moreover designed as removable, this enables a complete removal thereof when locking of the joint configuration is no longer necessary. The intervention for removing the locking element also takes place in a minimally-invasive manner in this case.

In a further embodiment of the method for installing a joint configuration, the joint body is connected via an adapter element to a first joint component.

Such a modular structure of the joint configuration with respect to a first joint component by way of the use of an adapter element enables the above-described advantageous use in an already implanted first joint component. Moreover, a removal of the joint configuration is not necessary if locking which can be disengaged or removed is used, which also reduces the stress to a patient.

In one particularly preferred embodiment, the adapter element has a support surface, which is brought into contact with the joint receptacle surface of the joint receptacle, and a catch, which prevents a relative rotation between the adapter element and the first joint component.

The adapter element therefore takes over the support of the joint body, while a relative rotation between the adapter element and the first joint component is prevented via the catch and thus any rotation between the joint body and the joint receptacle is transmitted directly to the first joint component.

In a further embodiment, the joint receptacle is fastened on a second joint component.

As already described above, in this way a revision of the second joint component which is not medically necessary can be prevented by simple retrofitting of the joint configuration.

BRIEF DESCRIPTION OF THE FIGURES

In the following figures, identical or identically-acting features are provided with identical reference numerals. In this case, the figures show a possible embodiment and the installation of a joint configuration. Proceeding therefrom, other embodiments are also explained hereafter, which also fall into the scope of protection of the claims. In particular:

DETAILED DESCRIPTION OF PREFERRED EMBODIMENTS

Figure 1:
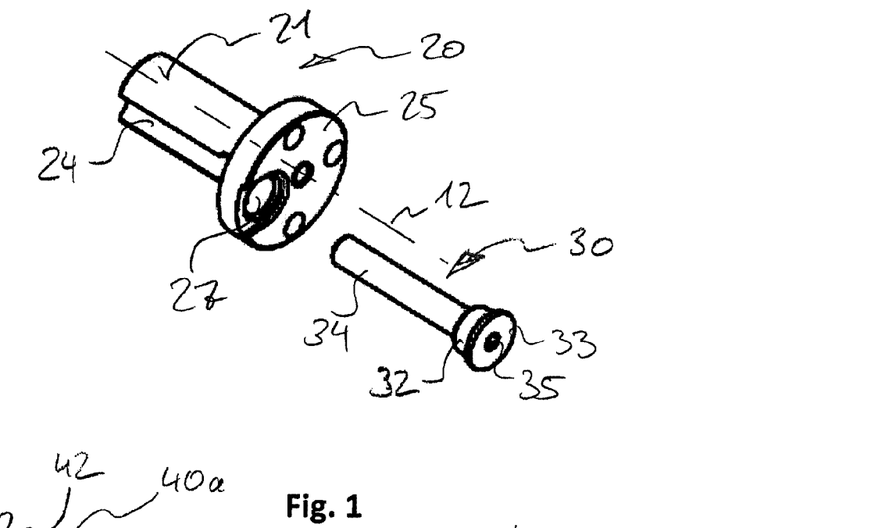
FIG. 1 shows a joint body with a locking element to be inserted.

FIG. 1 shows a possible embodiment of a joint body 20, into which a locking element 30 is insertable. The joint body 20 has a joint body surface 21, which forms a hinge joint, which is pivotable about an axis of rotation 12, together with a joint receptacle surface 11. The joint body surface is accordingly formed cylindrically having a circular cross section.

The joint body surface 21 has a body locking structure 24, which is provided in the exemplary embodiment shown in FIG. 1 as a recess, which extends into the joint body surface 21. As shown, the recess can extend over the entire width of the joint body surface 21. However, it is also possible that the recess extends only partially over the width of the joint body surface 21.

In another embodiment of the body locking structure 24, it can also be provided on the joint body 20 inside the joint body surface 21 or on at least one end face of the joint body 20.

In FIG. 1, the joint body 20 has a securing section 25 at one end, which is embodied as a flange in the present exemplary embodiment. This provides a defined insertion depth of the joint body 20 into a joint receptacle 10 (see FIG. 2), as described above.

Figure 2:
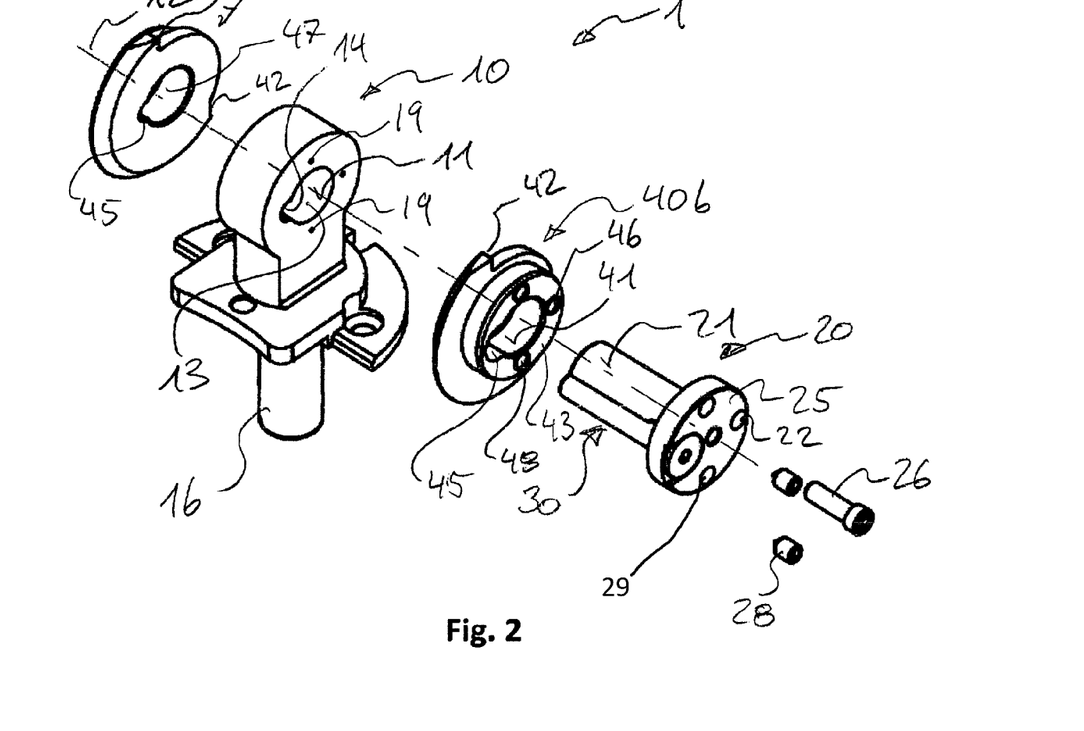
FIG. 2 shows a joint configuration with a joint receptacle and a joint body.

The locking element 30 which is also illustrated in FIG. 1 enables indirect locking of the body locking structure 24 and a receptacle locking structure 14 of the joint receptacle 10 (see FIG. 2). It is also possible to provide direct locking between the body locking structure and the receptacle locking structure. In such a case, the body locking structure and the receptacle locking structure are embodied as complementary to one another, and therefore a locking element is not necessary to effectuate locking between the joint body 20 and the joint receptacle 10.

The locking element 30 is insertable into the receptacle of the body locking structure 24 parallel to and at a distance from the axis of rotation 12 in the embodiment shown in FIG. 1. The recess of the body locking structure 24 is embodied as complementary to the shape of the locking element 30. In the exemplary embodiment shown, it has a partially-circular cross section.

Furthermore, the locking element 30 is insertable from the side into the body locking structure 24 on which the securing section 25 of the joint body 20 is provided. For this purpose, the securing section 25 formed as a flange has a passage hole 27. The passage hole 27 is preferably formed having a thread, into which a threaded section 32 of the locking element 30 engages, in order to secure the locking element 30 on the joint body 20. Unintentional disengagement of the locking is prevented by this securing.

The threaded section 32 preferably has a larger diameter than the locking section 34 of the locking element 30, which can be engaged via interlocking with the body locking structure 24. Furthermore, the locking element 30 has, on its rear end in the insertion direction behind the threaded section 32, a head 33, in which a tool engagement section 35 is provided for an engagement of a tool, in order to screw the threaded section 32 into the passage hole 27 of the joint body 20 provided with a thread.

FIG. 2, which illustrates one joint configuration 1, shows the locking element 30 described in FIG. 1 engaged with the body locking structure 24 of the joint body 20. As can be seen from FIG. 2, the joint body 20 is insertable into a passage hole 13 along the axis of rotation 12 of the joint. At least a part of the inner surface of the passage hole 13 forms the joint receptacle surface 11, which is movable in relation to the joint body surface 21 of the joint body 20 in the installed, unlocked state.

In the embodiment illustrated in FIG. 2, the joint receptacle surface 11 is interrupted by a recess, which forms the receptacle locking structure 14. This recess extends over the entire depth of the passage hole 13. As already described in conjunction with the body locking structure 24, however, an embodiment of the recess is also possible which extends over only a part of the depth of the passage hole 13. As already stated above, such an arrangement of the locking structures 14, 24 has the advantage of very stable locking with little play.

When the joint body 20 is therefore inserted into the joint receptacle 10, the locking element 30, which is engaged with both the body locking structure 24 and also with the receptacle locking structure 14 in the inserted state, enables locking of the hinge joint, which prevents a relative movement between the joint body 20 and the joint receptacle 10. If the locking element 30 is disengaged and/or removed, in contrast, a relative movement is possible between the joint body 20 and the joint receptacle 10, and therefore the joint configuration enables a normal function of the joint endoprosthesis.

Figure 3:
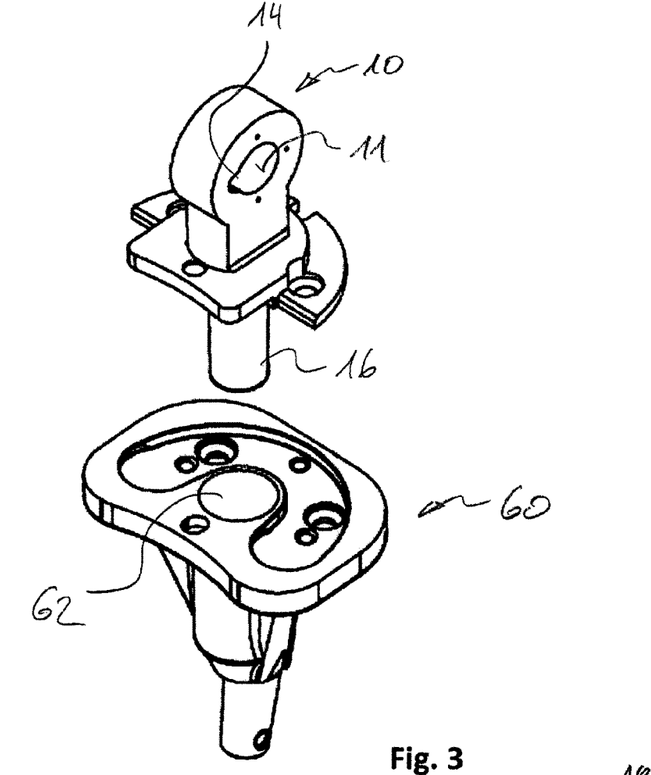
FIG. 3 shows the modular structure of a second joint component and a joint receptacle.
Figure 4:
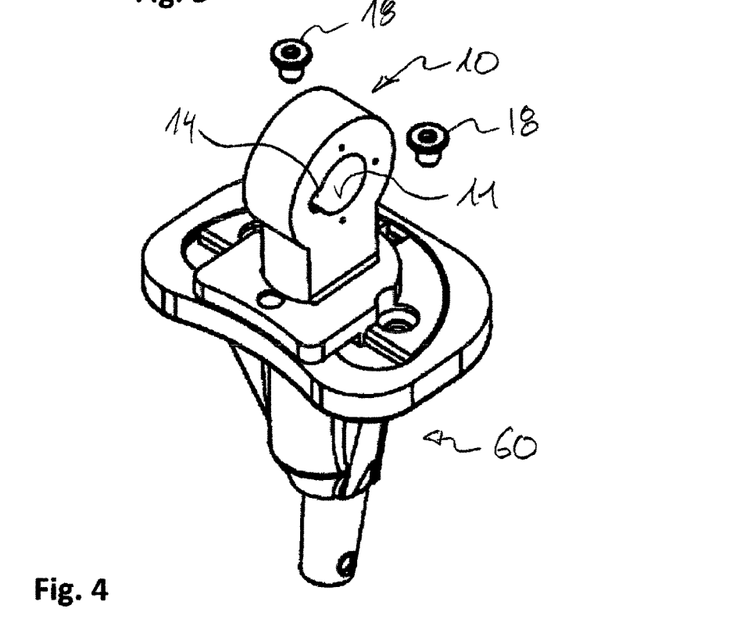
FIG. 4 shows the fastening of the joint receptacle on the second joint component.

As can furthermore be inferred from FIG. 2, the joint receptacle 10 has a connecting section 16, which, as described in greater detail hereafter, is used for establishing a connection to a second joint component 60 (see FIGS. 3 and 4). The exemplary embodiment of the joint receptacle 10 shown in FIG. 2 is a joint receptacle which is located on the tibial side of a knee joint replacement.

Furthermore, two adapter elements 40a, 40b are shown in FIG. 2, which are arranged on both sides of the passage hole of the joint receptacle 10. As described hereafter in conjunction with FIGS. 5 and 6, the adapter elements 40a, 40b are arranged or inserted laterally of the first joint component 50.

The adapter elements 40a, 40b have catches 42, which prevent a rotation about the axis of rotation 12 relative to the first joint component 50. Alternatively to the adapter elements described in greater detail hereafter, it is also possible to provide a first joint component 50, which, without adapter element, has a passage hole 47 integrated therein having a locking element recess 45.

The adapter element 40b has a stop surface 43 on the side facing toward the securing section 25, which touches the securing section 25 when the joint body 20 is inserted.

As can be seen in the embodiment shown of the adapter element 40b, it has a passage hole 47 having a locking element recess 45. The locking element recess 45 is embodied at least in sections in this case in such a way that it receives a part of the threaded section 32 of the locking element 30, but preferably does not form a threaded engagement with it.

The locking element recess 45 preferably tapers toward the side of the adapter element 40b opposite to the stop surfaces 43, as is recognizable in the second adapter element 40a in FIG. 2, and therefore only the locking section 34 of the locking element 30 is insertable thereafter. It is evident that the adapter element 40b can be embodied having a locking element recess 45 which is continuously provided only for receiving the locking section 34.

Although preferably a locking element recess 45 is provided for the locking section 34 in both adapter elements 40a, 40b, embodiments are thus nonetheless conceivable in which only the adapter element 40b located on the side of the securing section 25 has a locking element recess 45. However, more stable locking is possible if the locking section 34 is received in both adapter elements 40a, 40b, since the locking element 30 can be supported on both sides by the joint receptacle 10.

The adapter element 40b moreover has a receptacle 46 for a fastening element 26 in the stop surface 43 in the embodiment shown in FIG. 2. This receptacle 46 is preferably formed as a threaded hole. The fastening element 26, which secures the joint body 20 on the adapter element 40b via a passage hole 22 in the securing section 25 of the joint body 20, is insertable into the receptacle 46. It can be ensured in this way that in the unlocked state of the joint configuration 1, a relative movement is only possible between the joint receptacle surface 11 and the joint body surface 21.

As described above, this can be omitted in alternative embodiments. It is possible, for example, to secure the joint body at both ends, via securing sections 25 formed as flanges, in the passage hole 13 of the joint receptacle 10 and the passage hole 47 of the adapter elements 40.

As can furthermore be seen in FIG. 2, the locking element 30 is only insertable into the passage hole 27 of the joint body 20, the locking element recess 45 in the adapter element 40b, the receptacle locking structure 14, and the locking element recess 45 of the adapter element 40a when they assume a locking position, in which they are aligned with one another.

For the case in which the joint body 20 is connected directly to a first joint component 50 instead of via the adapter element 40, at least the receptacle locking structure 14 and the body locking structure 24 accordingly have to be aligned with one another and, if a locking element 30 is used, accordingly the recess in the first joint component 50 corresponding to the locking element recess 45.

The angle between the first joint component 50 and the second joint component 60 which the joint configuration 1 provides in the locked state is settable depending on the embodiment by a corresponding relative arrangement of the receptacle locking structure 14, the body locking structure 24, the locking element recess 45, and/or the catches 42 about the axis of rotation 12 in relation to one another.

In the illustrated embodiment, a setting of this angle is possible most simply by a corresponding arrangement of the catches 42 at the adapter elements 40a and 40b. Therefore, by way of appropriate placement of the catches 42 at the adapter elements 40a and 40b, different adapter elements can be provided for different locking angles.

In another or supplementary embodiment, it is possible, as already described above, to provide multiple receptacle locking structures 14 and/or body locking structures 24, in order to have multiple locking angles available for the locking for the joint endoprosthesis 90.

Two or three receptacle locking structures 14 are particularly preferably provided, which, as described, are still more preferably formed as a recess in the joint receptacle 11. For example, an operator can select a first receptacle locking structure 14 arranged for an extension of the limb or a second receptacle locking structure 14 arranged for a bending of the limb depending on the patient. It is also conceivable to select a locking position between an extension and a flexion of the joint, which can be advantageous, for example, for walking with a walking aid.

In order to find the locking position more easily intraoperatively by way of a relative movement between the joint receptacle surface 11 and the joint body surface 21, a centering means 28 can furthermore be provided, which perceptibly engages in a centering recess 19 of the joint receptacle 10 upon reaching the locking position. In the embodiment shown in FIG. 2, a centering pin is provided as the centering aid 28, which can latch through a centering passage hole 29 in the securing section 25 of the joint body 20 in a centering recess 19, which signals to an operator that the locking position has been reached and therefore the locking element 30 can be inserted.

The installation of the joint configuration 1 will be described in greater detail hereafter on the basis of a knee joint replacement, but can also be carried out on other joints, for example, an elbow joint.

The second joint component 60 illustrated in FIG. 3 is a tibia component, which can already be implanted in the knee of a patient or is to be implanted as a new implant during a retrofitting of the joint configuration 1 in the case of a retrofitting. For an installation of the joint configuration, in one step, after opening the knee joint, the connecting section of the joint receptacle 10 is inserted into a corresponding connecting section 62 of the second joint component 60. As can be seen in FIGS. 3 and 4, the installation of the joint receptacle 10 with the second joint component 60 takes place via interlocking and subsequent fixing using fastening elements 18. Alternatively, other fastening options of the second joint component 60 with the joint configuration 10 are also conceivable, for example, a cone connection.

Figure 5:
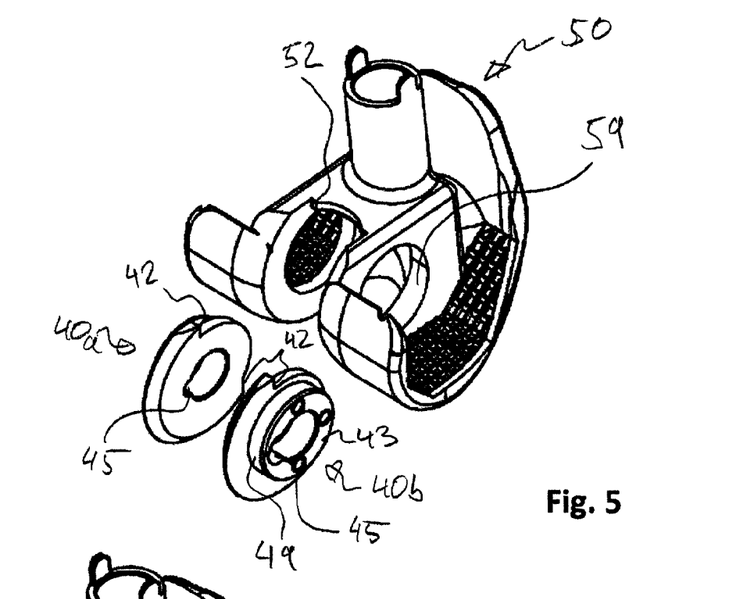
FIG. 5 shows two adapter elements insertable into a first joint component.
Figure 6:
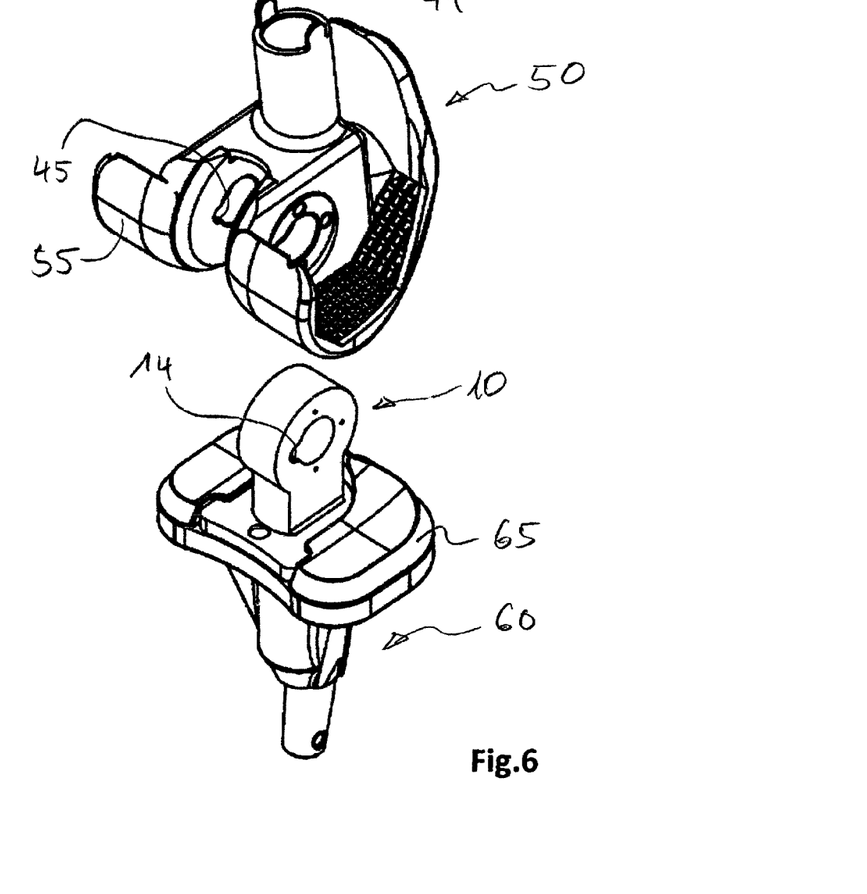
FIG. 6 shows a joint receptacle inserted into a second joint component and a first joint component to be installed therewith.

As described for the second joint component 60, the first joint component 50 shown in FIGS. 5 and 6 can also already be implanted, and therefore a previously existing joint configuration is replaced by the joint configuration 10, or is newly implanted together with the joint configuration 10.

The first joint component 50 shown in the exemplary embodiment in FIG. 5 is a femur component of a knee joint. Moreover, adapter elements 40a, 40b are used in the scope of the joint configuration 10. The joint configuration 10, as described above, is therefore a modular system, which can replace the joint configuration of a conventional joint endoprosthesis with the locked joint configuration 1 of the present invention.

In the present case, the adapter elements 40a, 40b are each inserted via a first insertion projection 49 into corresponding passage holes 59 of the first joint component 50. If the first joint component 50 is used with a conventional, non-lockable joint configuration, these passage holes 59 can be provided for a joint axis. The catches 42 of the adapter elements 40a, 40b are engaged during the insertion of the adapter elements 40a, 40b with corresponding catches 52 of the first joint element 50. As can be seen in FIG. 5, each adapter element 40 has two catches 42, which interact with two catches 52 of the first joint component, in order to fix the respective adapter element 40 in the corresponding passage hole 59 in the rotational direction.

The locking position and thus the angle between the first joint component 50 and the second joint component can preferably be established via the selection of the adapter elements 40, by providing the catches accordingly on the circumference of the adapter elements.

As is recognizable in FIGS. 5 and 6 on the basis of the locking element recess 45 positioned by the catches 42 and 52 and the receptacle locking structure 14, the exemplary knee joint replacement is in extension in the locked state. As already explained above, however, it can be advantageous to select another angle, for example, an angle at which the patient can assume a seated position.

FIG. 6 shows the first joint component 50 preinstalled with the adapter elements 40a, 40b and the second joint component 60 preinstalled with the joint receptacle 10 before the positioning thereof in relation to one another. As can be seen in FIG. 6, the first joint component 50 can have, in addition to the joint formed by the joint configuration 1, a further joint surface 55, which interacts in the installed state of the joint with a joint surface 65 installed on the second joint component.

Figure 7:
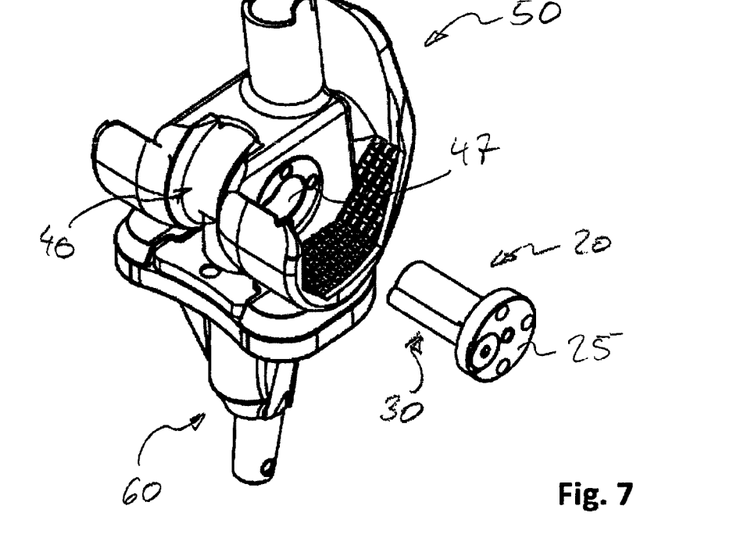
FIG. 7 shows a first and a second joint component, which are aligned in relation to one another for an insertion of a joint body and a locking element.

In FIG. 7, the first joint component 50 and the second joint component 60 are arranged in relation to one another in such a way that the passage hole 47 of the adapter elements 40a and 40b and the passage hole 13 of the joint receptacle 10 are aligned with one another. Therefore, in this state the joint body 20 can be inserted via the passage hole 47 of the first adapter element 40b, the passage hole 13 of the joint receptacle 10, and the passage hole 47 of the second adapter element 40a.

It is to be noted in this context that if the first joint component 50 is an already implanted joint component, bone tissue can be located in front of the passage holes 59 of the first joint component 50. Accordingly, a passage to at least one of the passage holes 59 has first to be provided intraoperatively. This is preferably carried out using a trephine, using which a bone cylinder having a diameter is removed laterally along the axis of rotation 12 of the joint, and therefore a free access results to the at least one passage hole 59 of the first joint component 50. After the installation, the removed bone cylinder can be inserted again, in order to reclose the access created to the respective passage hole 59.

In the embodiment shown in the figures, the securing of the joint body takes place via a single securing section 25 embodied as a flange. An access to one of the passage holes 59 is therefore sufficient to retrofit the joint replacement with the joint configuration 1. This has the advantage that the bone tissue and thus the patient are protected.

Furthermore, it can be inferred from FIG. 7 that the joint body 20 can be inserted with a locking element 30 already engaged. It is apparent that this is not necessary, but rather instead the locking element 30 can first be inserted when a locking of the joint is desired or also first the joint body 20 and then the locking element 30 are inserted for a locking.

If, as shown in FIG. 7, the joint body 20 and the locking element 30 are inserted in this manner, in the embodiment shown, in addition to the above-mentioned passage holes 47 and 13, the locking element recess 45 of at least one of the adapter elements 40a, 40b and also the receptacle locking structure 14 embodied as a recess also have to align accordingly, i.e., be located in the locking position.

Figure 8:
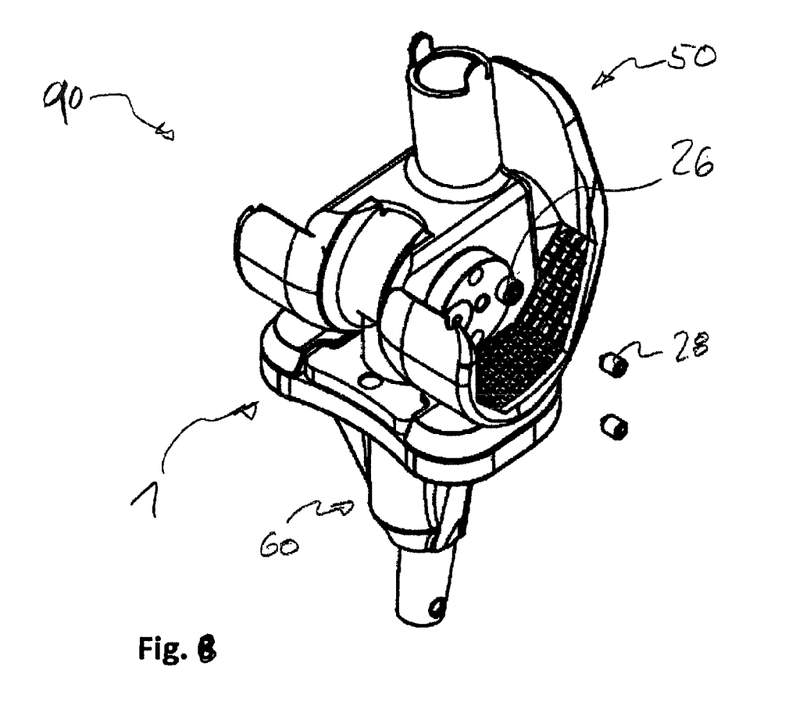
FIG. 8 shows an embodiment of a joint configuration which connects a first and a second joint component to one another.

FIG. 8 finally shows the joint configuration 1 in a state installed with the first joint component 50 and the second joint component 60. As can be seen, the joint body 20 is secured via the securing section 25 and the fastening element 26 on the first joint component 50. Consequently, in the embodiment shown, a relative movement is only possible between the joint receptacle surface 11 and the joint body surface 21 in the joint configuration 1.

This has the advantage, inter alia, that the joint formed by the joint configuration 1 is terminated from the bone side, and therefore a penetration of foreign particles into the joint is prevented. It is additionally possible, instead of a passage hole 47 in the adapter element 40a, which is opposite to the adapter element 40b, on which the securing section 25 of the joint body 20 abuts, to provide a pocket hole or also a cap, which again covers the passage hole 47 of the adapter element 40a. A penetration of foreign particles from the other side of the joint configuration 1 is thus also prevented.

Furthermore, FIG. 8 shows that the centering means can be removed. Alternatively or additionally, it is possible not to use the centering means as an aid in order to find the locking position, as described above, but rather instead to use them as additional securing elements against pivoting of the joint body 20 relative to the first joint component 50.

LIST OF REFERENCE NUMERALS 1 joint configuration
10 joint receptacle
11 joint receptacle surface
12 rotation center point
13 passage hole
14 receptacle locking structure
16 connecting section
18 fastening element
19 centering recess
20 joint body
21 joint body surface
22 passage hole for the fastening element 26
24 body locking structure
25 securing section
26 fastening element
27 passage hole
28 centering means
29 centering passage hole
30 locking element
32 threaded section of the locking element
33 head of the locking element
34 locking section
40a,b adapter element
41 support surface for joint body
42 catch
43 stop surface
44 support surface for locking element
45 locking element recess
46 receptacle for the fastening element 26
47 passage hole for receiving the joint body
48 receptacle for the centering means 28
49 insertion projection
50 first joint component
52 catch
55 joint surface of the first joint component
59 passage hole of the first joint component
60 second joint component
62 connecting section
65 joint surface of the second joint component
70 third joint component
80 fourth joint component
90 joint endoprosthesis

The invention claimed is:

1. A joint configuration (1) for a joint endoprosthesis (90) forming a hinge joint, comprising:
a joint receptacle (10), which has a joint receptacle surface (11) and a receptacle locking structure (14),
a joint body (20), which is receivable in the joint receptacle (10) and has a joint body surface (21) and a body locking structure (24),
wherein the joint receptacle surface (11) and the joint body surface (21) are movable relative to one another into a position in which the receptacle locking structure (14) and the body locking structure (24) assume a locking position, in which they can be engaged for a locked state between the joint receptacle (10) and the joint body (20), wherein
the joint receptacle comprises a passage hole (13) in which the joint body (20) is receivable, an inner surface of the passage hole (13) forming the joint receptacle surface (11), wherein the joint receptacle surface (11) is interrupted by a recess which forms the receptacle locking structure (14), and the recess extends at least over a part of the depth of the passage hole (13),
wherein the receptacle locking structure (14) and the body locking structure (24) can be engaged with a locking element (30), wherein the locking element (30) is insertable in the locking position into the receptacle locking structure (14) and the body locking structure (24), and
wherein the locking element (30) is fixable in relation to the joint body (20) via a threaded section (32).

2. The joint configuration according to claim 1, wherein the joint receptacle (10) has a connecting section (16) for a connection to a second joint component (60).

3. The joint configuration according to claim 1, comprising at least one further receptacle locking structure (14) and/or one further body locking structure (24), which is arranged in order to provide at least one further locking position for locking of the joint configuration.

4. The joint configuration according to claim 1, wherein the receptacle locking structure (14) adjoins the joint receptacle surface (11) and the body locking structure (24) adjoins the joint body surface (21).

5. The joint configuration according to claim 1, wherein the receptacle locking structure (14) is formed as a recess in the joint receptacle surface (11) and/or the body locking structure (24) is formed as a recess in the joint body surface (21).

6. The joint configuration according to claim 4, wherein the receptacle locking structure (14) is formed as a recess in the joint receptacle surface (11) and/or the body locking structure (24) is formed as a recess in the joint body surface (21).

7. The joint configuration according to claim 1, wherein the joint receptacle (10) and the joint body (20) are pivotable in relation to one another about an axis of rotation (12) and the locking element (30) is insertable substantially parallel to the axis of rotation (12).

8. The joint configuration according to claim 1, wherein the joint body (20) has a securing section (25) for securing the joint body (20) on a first joint component (50), wherein the securing section (25) is formed as a flange at one end of the joint body (20).

9. The joint configuration according to claim 8, wherein the securing section (25) is fastened using a fastening element (26) on the first joint component (50).

10. The joint configuration according to claim 8, wherein at least one adapter element (40) is provided between the joint body (20) and the first joint component (50), which has a support surface (41) for supporting the joint body surface (21).

11. The joint configuration according to claim 9, wherein at least one adapter element (40) is provided between the joint body (20) and the first joint component (50), which has a support surface (41) for supporting the joint body surface (21).

12. The joint configuration according to claim 10, wherein the adapter element (40) has a catch (42), which prevents a rotation between the adapter element (40) and the first joint component (50).

13. The joint configuration according to claim 11, wherein the adapter element (40) has a catch (42), which prevents a rotation between the adapter element (40) and the first joint component (50).

\* \* \* \* \*